United States Patent [19]

Hutchens et al.

[11] Patent Number: 5,707,923

[45] Date of Patent: Jan. 13, 1998

[54] METHOD OF AND APPARATUS FOR CONTROLLING AN ALKYLATION PROCESS

[75] Inventors: Brian Hutchens, Roeland Park, Kans.; Kevin E. Fitzgerald, Severna Park, Md.

[73] Assignee: Stratco, Inc., Leawood, Kans.

[21] Appl. No.: 432,084

[22] Filed: May 1, 1995

[51] Int. Cl.$^6$ ............................................................. C07C 2/56
[52] U.S. Cl. .......................... 502/956; 502/701; 502/709; 208/DIG. 1
[58] Field of Search .......................... 585/956, 709, 585/375, 701, 501, 401

[56] References Cited

U.S. PATENT DOCUMENTS

| | | | |
|---|---|---|---|
| 3,653,835 | 4/1972 | Brandel | 23/230 |
| 3,729,624 | 4/1973 | Hopkins et al. | 235/151.12 |
| 3,819,917 | 6/1974 | Sweeney, Jr. et al. | 235/151.12 |
| 3,864,346 | 2/1975 | Child et al. | 260/683.59 |
| 3,870,765 | 3/1975 | McCoy et al. | 260/683.51 |
| 3,956,417 | 5/1976 | Franz et al. | 260/683.63 |
| 3,970,721 | 7/1976 | Brockington et al. | 260/683.63 |
| 4,017,263 | 4/1977 | Holmes et al. | 23/288 E |
| 4,018,846 | 4/1977 | Mayer | 260/683.59 |
| 4,023,096 | 5/1977 | Schmidt | 324/61 R |
| 4,033,899 | 7/1977 | Bennett et al. | 252/420 |
| 4,049,739 | 9/1977 | Zabransky et al. | 260/671 R |
| 4,066,716 | 1/1978 | Herbstman et al. | 260/683.47 |
| 4,073,822 | 2/1978 | Mayer | 260/683.47 |
| 4,075,258 | 2/1978 | Caulk et al. | 260/683.44 |
| 4,113,657 | 9/1978 | Herbstman et al. | 252/442 |
| 4,180,696 | 12/1979 | Lewis, Jr. et al. | 585/717 |
| 4,209,656 | 6/1980 | Prescott et al. | 585/715 |
| 5,012,033 | 4/1991 | Child et al. | 585/722 |
| 5,157,195 | 10/1992 | Hovis et al. | 585/701 |
| 5,157,197 | 10/1992 | Cooper et al. | 585/726 |

OTHER PUBLICATIONS

"Emulsion Analyzer ESC 2000/2001", Robertshaw Controls Company, Industrial Instrumentation Division, Patent No. 4,023,096 issued to Shell Oil Company, May 10, 1977.
ELITE, "Model CMF050 Mass Flow and Density Sensor", Micro Motion Rosemount.

*Primary Examiner*—Glenn A. Caldarola
*Assistant Examiner*—Bekir L. Yildirim
*Attorney, Agent, or Firm*—J. M. Gilbreth; Robert W. Strozier; Gilbreth & Stozier, P.C.

[57] ABSTRACT

Disclosed is a method of alkylating in which a hydrocarbon and acid emulsion is circulated in a reaction loop between a reactor and a cooler. A small sidestream of the reaction emulsion is constantly removed to a liquid-liquid separator where the hydrocarbon and acid phases are separated. The recovered acid is then recycled back to the reaction loop. The amount of recovered acid recycled is controlled by monitoring the density of the reaction emulsion.

19 Claims, 1 Drawing Sheet in the United States.

METHOD OF AND APPARATUS FOR CONTROLLING AN ALKYLATION PROCESS

BACKGROUND OF THE INVENTION

1. Field of the Invention

The present invention relates to alkylation. In another aspect, the present invention relates to a method of and apparatus for controlling an alkylation process. In even another aspect, the present invention relates to a method of and apparatus for controlling an alkylation process by monitoring the specific gravity of the reaction emulsion mixture. In still another aspect, the present invention relates to a method of and apparatus for controlling the amount catalyst to be recycled back to the alkylation process by monitoring the specific gravity of the reaction emulsion mixture. In yet another aspect, the present invention relates to a method of and apparatus for detecting pre-warning signs of an alkylation process acid runaway by monitoring the specific gravity of the reaction emulsion mixture.

2. Description of the Related Art

Alkylation is a well known refinery process for converting light gaseous olefins into high-octane gasoline components. Very simply, alkylation involves the addition of an alkyl group to an organic molecule. Thus, an isoparaffin can be reacted with an olefin to provide an isoparaffin of higher molecular weight. Generally, the alkylation of isoparaffins with olefins is accomplished by contacting the reactants with an acid acting catalyst such as hydrogen fluoride or sulfuric acid, settling the mixture to separate the catalyst from hydrocarbons, and further separating the hydrocarbons, usually by fractionation to recover alkylate product. The resulting alkylate product is typically a mixture of $C_5$ to $C_{16}$ isomers, with the exact composition depending upon the particular isoparaffin and olefin reactants utilized, as well as alkylation process conditions.

Alkylation has recently been increasing in importance as a result of the curtailment in the use of tetraethyl lead as an octane-improving additive for gasoline, not only has the production of unleaded gasoline increased but the octane number specification of all grades of gasoline have increased as well.

Additionally, reformulated gasoline specifications require a reduction in both the Reid Vapor Pressure ("RVP") and the olefin content. Alkylate is a low vapor pressure, high octane gasoline blending component containing substantially no olefins. Thus, alkylate helps refiners meet the new reduced RVP and reduced olefin content specifications. Additionally, alkylate burns cleanly, resulting in lower levels of undesired emissions from gasoline engines. In fact, because of its usefulness eliminating lead and in meeting the new reformulated gasoline specifications, alkylate typically comprises 10–15% of the gasoline pool.

Isoparaffin-olefin alkylation processes have become the key route to the production of these highly branched paraffin octane enhancers which are blended into gasolines.

As practiced commercially, alkylation most commonly involves reacting isobutane, with $C_3$ to $C_5$ olefins in the presence of an acid catalyst, typically either hydrofluoric acid or sulfuric acid. The resulting alkylate product comprises predominately $C_7$ to $C_9$ isoparaffins, along with lesser amounts of lighter and heavier isoparaffins in the $C_6$ to $C_{12}$ range, and some isopentane.

A typical commercial unit will react an isoparaffin with an olefin in the presence of the acid catalyst, forming an acid-hydrocarbon mixture which is sent to a settler where the hydrocarbon is separated from the acid. A portion of the acid is recycled while the remaining acid is discharged from the alkylation unit. Fresh acid is added to the recycled acid to affect the strength of the acid.

Two variables which may be used to control an alkylation process includes the strength of the acid catalyst and the inventory of acid remaining in the system. The inventory of acid is generally utilized to control the recycle rate of the acid, while the strength of acid determines the amount of fresh acid to be added to the process.

Historically, it has been customary to obtain a small sample of the alkylation emulsion in a sight glass and allow it to stand until the acid settles, usually on the order of 30 to 40 minutes. The desired emulsion information is obtained by manually timing the settling and visually observing the percentage of acid in the emulsion. Based on these physical measurements, the alkylation process could then be adjusted to obtain optimum results.

This sight glass method suffers from several disadvantages.

Sight glasses are normally designed to include ball check valves which prevent the contents of the vessel from entering the atmosphere upon the sight glass breaking. In the case of the ratio glass used in monitoring alkylation processes, the ball check valves are generally removed as they restrict flow which interferes with obtaining a representative sample, and by-products of the alkylation process tend to plug the restricted ports in the ball check valves. While removal of the ball check valve can improve the operation of the sight glass, rupture of the sight glass from over pressuring, mechanical failure, improper installation or other reasons, creates the potential for an emulsion spill.

Additionally, the accuracy and repeatability of the ratio glass varies from operator to operator. It is the experience of the inventors that most operations personnel do not understand the calibration range of the sight glass and therefore, most readings from the ratio glass are inaccurate. And while the inventors believe that sight glass readings should be taken at least two times a day, it is their experience that because of the difficulty and nuisance of taking sight glass readings, most operators take sight glass readings only after they are experiencing alkylation problems, rather than taking readings to monitor such problems before they happen.

Even with constant readings, the sight glass requires a settling time of about 30 to 40 minutes, which restricts how many readings can be taken, and also means there is an informational delay as the data is about 30 to 40 minutes old by the time the sight glass can be read. Typically, if the emulsion requires more than 40 minutes, the system has a "tight" emulsion, i.e., high amount of acid. If the emulsion requires less than 10 minutes, the emulsion is probably hydrocarbon continuous.

There has been an attempt in the art to improve over the sight glass method of obtaining alkylation emulsion information. U.S. Pat. No. 4,023,096, issued May 10, 1977 to Schmidt discloses a method and apparatus for determining physical characteristics of emulsions. The U.S. Pat. No. '096 patent discloses a modified gravity or centrifugal settling cell having electrical capacitor plates disposed within the cell such that as the emulsion separates relative proportional areas of both of the plates are exposed to the components of the emulsion. The strength of the acid, as well as the settling time of the emulsion is determined by measuring the capacitance of the cell. The capacitance will vary exponentially and reach a steady state condition which will remain substantially constant. The settling time is related to the time required for the capacitance to reach steady state, while the acid strength is related to the magnitude of the capacitance in its steady state condition. While the U.S. Pat. No. '096 patent apparatus eliminates the need for an operator to read a sight glass, it still requires a certain settling time between readings. As noted above, the settling time limits the frequency at which samples can be taken, and causes an informational delay.

Even with the U.S. Pat. No. '096 apparatus, utilization of a sight glass is still the most common method of obtaining alkylation emulsion information.

In addition to the problem of determining the amount of spent catalyst to recycle, an independent and important problem is to maintain watch for an acid "run-away".

When using an acid catalyst in the alkylation of an olefin with an isoparaffin, an acid "run-away" can occur without warning as the acid starts dropping in acidity very rapidly. If the acidity of the system acid drops below a certain minimum, the alkylation reaction ceases and the acidity of the acid drops rapidly. If the run-away is not detected almost immediately, the acidity may drop so fast, and so far, that it becomes necessary to remove the acid from the system. At the same time, the alkylate product usually becomes contaminated with sulfur compounds in the form of alkyl sulfates. Thus, when such a condition occurs, acid and alkylate must be discarded and therefore are lost, or they must be further processed to make them suitable for use.

Generally, in commercial alkylation, if an abnormally fast drop in acidity is detected before the acidity drops below the minimum acidity, the acidity can usually be brought back to or above the minimum acidity by increasing the fresh acid feed and/or by decreasing or shutting off the olefin feed.

An acid run-away can be directly detected by monitoring the acidity of the acid.

Unfortunately, a major difficulty, especially in commercial operation, is that there is usually no continuous monitoring of the acidity, with the result that a matter of hours may elapse between the time a sample is taken and analytical data on acidity are obtained. Thus, by the time test results are obtained, the acidity may already be so low that the acid is no longer an alkylation catalyst. The result is that no matter how much fresh acid is charged, within the capacity of the reactor and settler, and ever if olefin feed is cut out, the acidity cannot be raised to a point at which the acid will again act as an alkylation catalyst.

For example, prior art methods for monitoring alkylation catalyst acidity having included spectrophotometry, which suffers from the necessity of using relatively expensive spectrophotometers, and suffers from the need for the continuous addition of an indicator compound such as alizarin blue thus requiring a complicated and expensive indicator control and metering system.

Another acidity monitoring system is disclosed in U.S. Pat. No. 3,653,835, issued Apr. 4, 1972 to Brandel in which an acid sample is pumped by a first pump from the settler acid recycle line to a stripping chamber where volatile hydrocarbons are vaporized through a vent tube, the stripped sample then enters a settling chamber where high molecular weight hydrocarbons are skimmed off by an overflow tube, with the purified acid then pumped by a second pump into a hydrometer pot for analysis. The U.S. Pat. No. '835 system is somewhat complex and requires a constant temperature bath for maintaining the sample at the stripping temperature, vent tube, settler, skimming tube as well as two pumps. In addition to controlling the temperature, the pumping rates of the two pumps must be controlled.

The present inventors also suggest that monitoring the change and/or rate of change in the acid to hydrocarbon ratio in the reaction emulsion can serve as a run-away warning method. However, while the reaction emulsion acid/hydrocarbon ratio can be monitored by the prior art sight glass methods, such sight glass methods have several disadvantages as described above, including accuracy, repeatability, settling time, as well as others.

Thus, there is a need in the art for an improved alkylation process.

There is also a need in the art for an improved apparatus for and method of determining the amount of spent acid catalyst to recycle in the alkylation process.

There is another need in the art for an improved apparatus for and method of determining the amount of spent acid catalyst to recycle in the alkylation process which does not suffer from the time lag of the prior art apparatus and methods.

There is even another need in the prior art for an improved apparatus for and method of monitoring the acid to hydrocarbon ratio for the purpose of detecting an acid run-away.

These and other needs of the art will become evident to those of skill in the alkylation art upon reading this specification.

SUMMARY OF THE INVENTION

It is an object of the present invention to provide for an improved alkylation process.

It is also an object of the present invention to provide for an improved apparatus for and method of determining the amount of spent acid catalyst to recycle in the alkylation process.

It is another object of the present invention to provide for an improved apparatus for and method of determining the amount of spent acid catalyst to recycle in the alkylation process which does not suffer from the time lag of the prior art apparatus and methods.

It is even another an object of the present invention to provide for an improved apparatus for and method of monitoring the acid to hydrocarbon ratio for the purpose of detecting an acid run-away.

These and other objects of the present invention will become evident to those of skill in the alkylation art upon reading this specification.

According to the present invention there is provided a method of controlling the alkylation of an emulsion mixture of hydrocarbons and an acid catalyst in a reaction zone, which alkylation produces an emulsion product stream of alkylated hydrocarbons and the acid catalyst, which product steam is then separated into a hydrocarbon product steam and a recycle acid steam, wherein a recycle percentage, of the recycle acid steam is recycled to the reaction zone. The method generally includes first inputting upper and lower operating setpoint values into a controller, wherein the setpoint values are representative of density, mole, volume or weight operating limits for the acid or hydrocarbons in the emulsion mixture. The method also includes recovering a portion of the emulsion mixture as an emulsion sample. The method further includes determining the density of the emulsion sample while it is in an emulsion state. The method even further includes inputing the density of the emulsion sample into the controller. Next, the method includes correlating the density of the emulsion sample to the upper and lower setpoint values. Finally, the method includes outputting from the controller an indication that the recycle percentage should be increased if the density of the emulsion sample correlates to a value above the upper setpoint value, and an indication that the recycle percentage should be decreased if the density of the emulsion sample correlates to a value below the lower setpoint value.

DETAILED DESCRIPTION OF THE INVENTION

Figure 1:
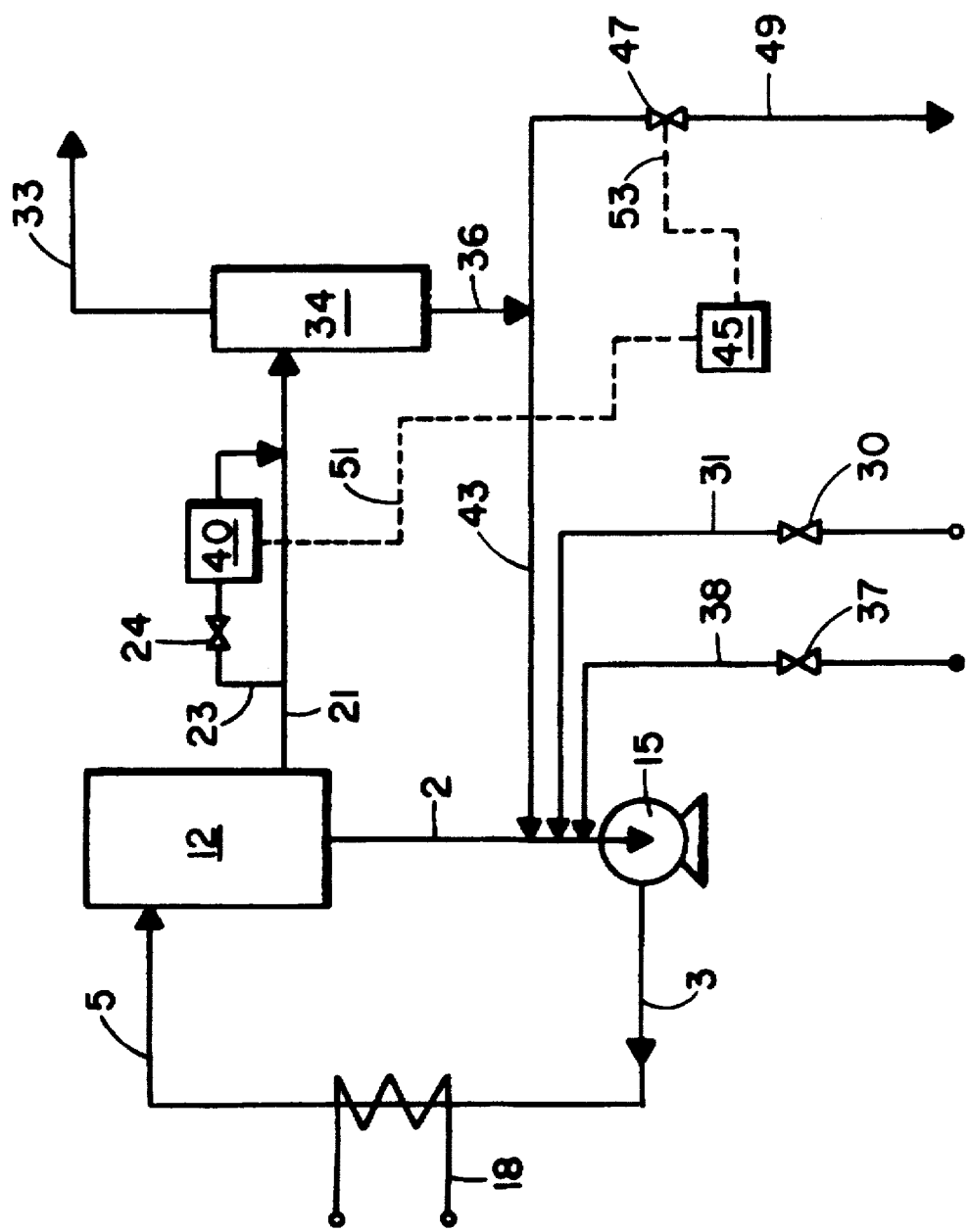
FIG. 1 is a schematic representation of one embodiment of the invention of the present invention showing reactor 12, circulation pump 15, cooler 18, liquid-liquid separator 34, density measuring device 40 and controller 45.

Alkylation processes in general are well known to those of skill in the art. For example, see "Catalytic Alkylation", Petri/Chem Engineer, December 1961 and January 1962, "Alkylation will be key process in reformulated gasoline era", Oil & Gas Journal, Nov. 12, 1990, pp. 79–92, "$H_2SO_4$, HF processes compared, and new technologies revealed", Oil & Gas Journal, Nov. 26, 1990, pp. 70–77, and "Which alkylation—HF or $H_2SO_4$?", Hydrocarbon Processing, September 1985, all herein incorporated by reference. Additionally, alkylation is generally disclosed in U.S. Pat. Nos. 4,018,846; 4,225,740; 4,276,731; 4,371,731; 4,383,977; 4,404,418; 4,467,131; 4,513,165; 4,777,323, and 5,157,196; all herein also incorporated by reference.

In the alkylation process of the present invention, a large stream of hydrocarbons undergoes alkylation in the presence of an acid catalyst. An emulsion of the hydrocarbons and the catalyst is continuously circulated between a reaction zone and a cooling zone, with a small portion of the reaction emulsion continuously removed to a liquid-liquid separator where the hydrocarbons and catalyst are separated. The hydrocarbons recovered from the liquid-liquid separator include alkylate, propane and n-butane, which are later separated, generally by fractionation. The catalyst recovered from the liquid-liquid separator is either discarded, or all or a portion of the catalyst is recycled to the reaction zone. The amount of catalyst to be recycled is dependent upon the density of the reaction emulsion, which is monitored.

According to the present invention, the density of the reaction emulsion is first determined. Control of the alkylation reaction acid recycle is accomplished by correlating the emulsion density to the ratio of hydrocarbons to catalyst in the reaction emulsion. Of course, as specific gravity is a ratio of the emulsion density to water density, specific gravity may also be utilized in the practice of the present invention.

The emulsion density may be determined by any suitable method and by any suitable apparatus. As an improvement over prior art methods of controlling alkylation reactions, the emulsion density is preferably determined while the hydrocarbon/catalyst mixture is in an emulsion state, that is prior to any settling or separation. The emulsion density can be determined on an emulsion sample batch wise, that is from a now flowing emulsion mixture. An alternate and preferred method is to determine the emulsion density from a flowing emulsion stream, in which case, an in-line density measurement device is utilized. By its very nature, "in-line" would of course mean that the device is suitable for measuring the density of the emulsion, without a need for first settling the emulsion. Such a device must provide accurate measurement of the density while not generating too substantial of a pressure drop. Preferably, the density measuring device will provide readings with a minimal amount of time between readings. A non-limiting example of suitable in-line density measurement device includes the Model CMF050 Mass Flow and Density Sensor available from Micro Motion of Boulder Colo.

Once the density of the emulsion is determined, the density measurement must be correlated to the liquid volume ratio of acid to hydrocarbon in the emulsion reaction. The density of various volume ratios of acid to mixtures of hydrocarbons is easily determined through experimental procedures. This relationship of density to volume ratios can then be utilized in table or graph form, or even stored in a computer look-up file. Once the density of the emulsion is obtained, the corresponding volume ratio is determined either from a table or graph, or from a computer look-up file. This volume ratio is then compared to the desired volume ratio operating range, with adjustments made accordingly.

At a minimum, the liquid volume of acid in the reaction emulsion must be suitable to avoid a hydrocarbon continuous emulsion. At the upper limit, the liquid volume of the acid in the reaction emulsion is generally selected to provide proper hydraulics and mixing performance in the reaction zone. Generally, some reactors may be operated at a liquid volume of acid in the emulsion reaction as low as about 40 volume percent, and some reactors may be operated at a liquid volume of acid in the emulsion reaction as high as about 65 volume percent. However, it must be understood that each unit will have its own optimum based on the feed stoichiometry, and it is hard to place a particular range on this variable. However, with the reactors operated by the inventors, they have generally found that the liquid volume of acid in the reaction emulsion is maintained in the range of about 45 volume percent to about 60 volume percent. Preferably for their reactors, the liquid volume of acid in the reaction emulsion is maintained in the range of about 50 volume percent to about 60 volume percent, and most preferably maintained in the range of about 50 volume percent to about 55 volume percent.

The density or specific gravity of the reaction emulsion is a function of the acid strength, temperature, hydrocarbon composition and acid diluents. The inventors have determined that acid strength has the most affect on specific gravity, with temperature being quite minimal (0.00086 per °F.), with acid diluents and hydrocarbon composition even less significant so as to be considered negligible.

Thus, for a given operating temperature or range, the density or specific gravity of the acid at a given strength and of the reactor effluent are weighted based on volume percentage, to obtain a weighted density. A lower density number corresponding to a lower operating acid volume, and a higher density number corresponding to an upper operating acid volume are both calculated to establish the operating ranges. An acid density reading above the upper limit indicates that too much acid is being recycled, and that some acid should be removed from the alkylation unit. An acid density reading below the lower limit indicates that too little acid is being recycled, and that less acid should be removed from the alkylation unit. The acid reading can also be used to make adjustments in the acid recycle rate as the acid reading approaches each of these upper and lower limits.

The above embodiment generally includes determining the emulsion density, determining the volume ratio from the density, and then comparing the determined volume to the desired volume operating range, with adjustments made accordingly. As an alternative method, it is also possible to convert the desired volume operating range into a desired density operating range. Thus, another embodiment of the method of the present invention would include determining the emulsion density, and then comparing the determined density to the desired density operating range, with adjustments made accordingly.

The present invention will now be explained by reference to FIG. 1, which is a schematic drawing showing reactor 12, circulation pump 15, cooler 18 and liquid-liquid separator 34. In operation, hydrocarbon reactants are introduced to line 2 through line 31 controlled by valve 30, with acid catalyst introduced to line 2 through line 38 controlled by valve 37. Circulation pump 15 circulates a reaction emulsion between cooler 18 and alkylation reactor 12 through lines 2, 3, and 5 as shown in FIG. 1. During operation, a small side stream 21 of the emulsion reaction mixture is routed to liquid-liquid separator 34 where the acid and hydrocarbon components of the emulsion are separated. Hydrocarbon components are removed via line 33. The acid component is recycled back to the alkylation line 2 via lines 36 and 43 as shown in FIG. 1. The amount of acid recycled is controlled by valve 47. Excess acid recycle is removed from the system by opening valve 47 with excess acid exiting the system through line 49.

According to the present invention, a density measuring device 40 is installed in line 23, a sidestream off of line 21. As explained above, density measuring device 40 is preferably an in-line measuring device. Opening valve 24 will allow the emulsion mixture from line 21 to be sampled by density measuring device 40.

It is understood that the density data from density measuring device 40 may be obtained by the operator, compiled in a recording device, or even input directly into a computer or process controller. As shown in FIG. 1, density measuring device is connected via wire 51 to computer 45.

Into computer 45 will be input set points of either the upper and lower operating densities for the reaction emulsion in reactor 12, or the upper and lower operating percent volumes or volume ratios for the reaction emulsion in reactor 12.

When the operating percent volumes or volume ratios are utilized as set points, computer 45 will utilize some scheme to relate the emulsion density to liquid volumes of the hydrocarbon mixture and acid catalyst. For example, computer 45 may utilize a look-up table relating emulsion density to the liquid volume ratio of hydrocarbons to acid catalyst. Alternatively, the computer my utilize some mathematical relationship to relate emulsion density to the liquid volumes of hydrocarbons and acid catalyst. Of course, the relationship between emulsion density and the percent volume of the components will vary slightly with the type of catalyst and hydrocarbons utilized in the emulsion.

Once density data is obtained, recycle control valve 47 may be controlled by an operator or by a computer or process controller. As shown in FIG. 1, recycle control valve is connected via wire 53 to computer 45.

Based on the emulsion density reading from density measuring device 40, recycle valve 47 may be controlled utilizing any type of control scheme, including proportional, integral, differential control schemes or any combination of the foregoing.

While density measuring device 40 is shown in FIG. 1 as being located in sidestream 23 off of stream 21, it is to be understood that density device 40 may be located in any position suitable to obtain density readings of the reaction emulsion. For example, density measuring device 40 could be located in-line in lines 2, 3, 5 or 21, or in sidestreams connected to lines 2, 3, 5 or 21. Furthermore, density measuring device 40 could be connected directly to reactor 12.

In the practice of the alkylation process of the present invention, the precise process steps and process conditions will vary somewhat depending upon the catalyst system utilized, the alkylate product desired, available equipment, process economics and other factors. It is anticipated that any suitable catalyst may be utilized. The preferred types of catalysts are liquid or gaseous catalysts.

In the practice of the present invention, the reacting hydrocarbons may include $C_3$ to $C_5$ olefins as well as $C_4$ to $C_5$ paraffins.

The alkylation process of the present invention is generally operated with ratios of isoparaffin to olefin in the feed streams to the reactor of greater than 1 to minimize undesired polymerization reactions. The isoparaffin to olefin ratio is generally in the range of about 2:1 to about 50:1, and preferably in the range of about 4:1 to about 20:1. Most preferably for hydrogen fluoride catalyzed alkylation, the isoparaffin to olefin ratio is in the range of about 10:1 to about 15:1. Most preferably for sulfuric acid catalyzed alkylation, the isoparaffin to olefin ratio is in the range of about 5:1 to about 10:1.

For the present invention the alkylation is generally carried out by contacting the catalyst and the reacting hydrocarbons in a reactor under closely controlled conditions. Alkylation reactions are very exothermic and require cooling to remove the heat of reaction from the reactor.

Reactor systems useful in the practice of the present invention include time-tank or pipe reactors, the Stratco® Contactor reactor, cascade reactors, gravity reactors, solid catalyst reactors, and the like, and other types of alkylation reactors known to those of skill in the alkylation art.

The catalyst and the reacting hydrocarbons are generally contacted together in the reactor utilizing a sufficient level of agitation to provide intimate contact between the two liquid phases. High levels of agitation are generally more important for sulfuric acid alkylation than for HF alkylation. The agitation is generally provided utilizing baffling, positioning of the impeller and by recycle streams.

Additionally, with some reactor systems, the hydrocarbons may be contacted with a liquid catalyst in the form of a fine dispersion in the liquid catalyst. The hydrocarbon droplet size utilized will be in the range of about 10 to about 1000 microns, preferably about 10 to about 100 microns to give good contact with the catalyst. The fine dispersion of hydrocarbons may be obtained by any suitable method, including introducing the hydrocarbons into the reactor at high velocity through nozzles, by utilizing a high shear mechanical device such as a centrifugal pump, by utilizing a static mixer, or by any other suitable method.

The alkylation catalyst utilized in the present alkylation invention may be any catalyst that will catalytically effect the reaction of the paraffins and olefins. Non-limiting examples of suitable catalysts include strong acid catalysts such as hydrofluoric acid, sulfuric acid, phosphoric acid, mixtures of sulfuric and phosphoric acids, metal halides such as aluminum chloride or aluminum bromide, certain complexes of aluminum chloride and sulfuric acid, and the like.

Acid strength of the catalyst utilized in the present invention is generally maintained high enough to avoid dilution of the acid catalyst but low enough to avoid excessive side reactions. For example, the range of useful strengths of sulfuric acid is generally in the range of about 86 to about 99 weight percent.

The volume ratio of catalyst to total hydrocarbons is generally in the range of about 10:1 to about 1:10, and preferably in the range of about 10:1 to about 1:2.

The alkylation temperature and pressure utilized in the present invention is generally selected to yield the desired alkylation products without undue detrimental effects upon the catalyst or alkylation reactants.

Generally, the alkylation temperature utilized in the present invention is in the range of about −60° F. to about 1000° F. Preferably, the alkylation temperature utilized in the present invention is in the range of about −40° F. to about 200° F., more preferably in the range of about 35° F. to about 200° F., and most preferably in the range of about 35° F. to about 125° F. It is observed that at lower temperatures the rate of reaction is generally slower, and at higher temperatures, some cracking, polymerization and carbon formation occurs. The alkylation temperature utilized will generally also be influenced by economy of equipment and operating costs.

Additionally, it is also noted that the most preferred alkylation temperatures will also vary depending upon the type of catalyst utilized. The upper limit on the alkylation temperature is generally selected to avoid undue temperature degradation of the catalyst and to keep the catalyst in the desired state. For example, with sulfuric acid catalysts, the alkylation temperature is most preferably in the range of about 40° F. to about 50° F. and generally requires some type of refrigeration, while the most preferable alkylation temperature when utilizing hydrogen fluoride catalysts is in the range of about 85° F. to about 115° F., which can generally be maintained utilizing cooling water.

The alkylation pressure utilized in the present invention is generally selected to maintain at least a portion of, and preferably a majority of, the hydrocarbon reactants in a liquid phase. Generally, the reaction pressure is in the range of about atmospheric to about 5000 psi or more, preferably in the range of about 45 psi to about 1000 psi, and most preferably in the range of about 45 psi to about 250 psi.

Although the residence time of the reactants in the reactor or reaction zone can vary widely depending upon the process variables, the residence time is generally in the range of about 0.01 minutes to about 100 minutes. Preferably, the residence time is in the range of about 0.1 minutes to about 30 minutes, and more preferably in the range of about 1 minutes to about 20 minutes, and most preferably in the range of about 5 minutes to about 20 minutes.

EXAMPLES

Calculated Example 1

For this example, it is assumed that at the lower limit that 90 wt % $H_2SO_4$ is utilized, that at the upper limit 97 wt % $H_2SO_4$ is utilized, that the acid volume percent operating ranges are from 45 to 60 volume percent.

The specific gravities of the acid and hydrocarbon components are shown in TABLE 1 as follows:

TABLE 1

| Component SG's | |
| --- | --- |
| Component | Specific Gravity (SG) |
| 90 wt % $H_2SO_4$ | 1.7250 |
| 97 wt % $H_2SO_4$ | 1.8300 |
| reaction effluent | 0.6300 |

The high and low specific gravities are calculated in the following TABLE 2 as follows:

TABLE 2

| Calculations | | | |
| --- | --- | --- | --- |
| LV % Acid in Effluent | Acid Strength (wt %) | Calculation | Specific Gravity |
| 45 | 90 | (0.45*1.7250) + (0.55*0.6300) | 1.1228 |
| 45 | 97 | (0.45*1.8300) + (0.55*0.6300) | 1.1700 |
| 60 | 90 | (0.60*1.7250) + (0.55*0.6300) | 1.2870 |
| 60 | 97 | (0.60*1.8300) + (0.55*0.6300) | 1.3500 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

We claim:

1. A method of controlling the alkylation of an emulsion mixture of hydrocarbons and an acid catalyst in a reaction zone, which alkylation produces an emulsion product stream comprising alkylated hydrocarbons and the acid catalyst, which product steam is then separated into a hydrocarbon product steam and a recycle acid steam, wherein a recycle percentage, of the recycle acid steam is recycled to the reaction zone, the method comprises:

(a) inputting upper and lower operating setpoint values into a controller, wherein the setpoint values are representative of density, mole, volume or weight operating limits for the acid or hydrocarbons in the emulsion mixture;

(b) recovering a portion of the emulsion mixture as an emulsion sample;

(c) determining the density of the emulsion sample while it is in an emulsion state;

(d) inputing the density of the emulsion sample into the controller;

(e) correlating the density of the emulsion sample to the upper and lower setpoint values;

(f) outputting from the controller an indication that the recycle percentage should be increased if the density of the emulsion sample correlates to a value above the upper setpoint value, and an indication that the recycle percentage should be decreased if the density of the emulsion sample correlates to a value below the lower setpoint value.

2. The method of claim 1 wherein in step (e) a formula is utilized to correlate the density of the emulsion sample to the upper and lower setpoint values.

3. The method of claim 1 wherein in step (e) a computer lookup table is utilized to correlate the density of the emulsion sample to the upper and lower setpoint values.

4. The method of claim 1 wherein in step (c) an in-line device is utilized to determine the density of the emulsion sample.

5. The method of claim 4 wherein in step (e) a computer lookup table is utilized to correlate the density of the emulsion sample to the upper and lower setpoint values.

6. The method of claim 4 wherein in step (e) a formula is utilized to correlate the density of the emulsion sample to the upper and lower setpoint values.

7. The method of claim 5 further comprising:

(g) adjusting the recycle percentage in response to the indication from step (f).

8. The method of claim 6 further comprising:

(g) adjusting the recycle percentage in response to the indication from step (f).

9. The method of claim 1 further comprising:

(g) adjusting the recycle percentage in response to the indication from step (g).

10. A method of controlling the alkylation of an emulsion mixture of hydrocarbons and an acid catalyst in a reaction zone, which alkylation produces an emulsion product stream of alkylated hydrocarbons and the acid catalyst, with a makeup acid stream providing acid to the reaction zone, the method comprises:

(a) inputing upper and lower operating setpoint values into a controller, wherein the setpoint values are representative of density, mole, volume or weight operating limits for the acid or hydrocarbons in the emulsion mixture;

(b) recovering a portion of the emulsion mixture as an emulsion sample;

(c) determining the density of the emulsion sample while it is in an emulsion state;

(d) inputing the density of the emulsion sample into the controller;

(e) correlating the density of the emulsion sample to the upper and lower setpoint values;

(f) outputting from the controller an indication that the amount of makeup acid should be increased if the density of the emulsion sample correlates to a value above the upper setpoint value, and an indication that the amount of makeup acid should be decreased if the density of the emulsion sample correlates to a value below the lower setpoint value.

11. The method of claim 10 wherein in step (e) a formula is utilized to correlate the density of the emulsion sample to the upper and lower setpoint values.

12. The method of claim 10 wherein in step (e) a computer lookup table is utilized to correlate the density of the emulsion sample to the upper and lower setpoint values.

13. The method of claim 10 wherein in step (c) an inline device is utilized to determine the density of the emulsion sample.

14. The method of claim 13 wherein in step (e) a computer lookup table is utilized to correlate the density of the emulsion sample to the upper and lower setpoint values.

15. The method of claim 13 wherein in step (e) a formula is utilized to correlate the density of the emulsion sample to the upper and lower setpoint values.

16. The method of claim 14 further comprising:

(f) adjusting the recycle percentage in response to the indication from step (g).

17. The method of claim 15 further comprising:

(f) adjusting the recycle percentage in response to the indication from step (g).

18. The method of claim 10 further comprising:

(f) adjusting the recycle percentage in response to the indication from step (g).

19. A method of controlling the alkylation of an emulsion mixture of hydrocarbons and an acid catalyst in a reaction zone, which alkylation produces an emulsion product stream of alkylated hydrocarbons and the acid catalyst, with a makeup acid stream providing acid to the reaction zone, wherein the makeup acid steam comprises acid from product stream and fresh acid, the the method comprises:

(a) inputing upper and lower operating setpoint values into a controller, wherein the setpoint values are representative of density, mole, volume or weight operating limits for the acid or hydrocarbons in the emulsion mixture;

(b) recovering a portion of the emulsion mixture as an emulsion sample;

(c) determining the density of the emulsion sample while it is in an emulsion state;

(d) inputing the density of the emulsion sample into the controller;

(e) correlating the density of the emulsion sample to the upper and lower setpoint values;

(f) outputting from the controller an indication that the amount of makeup acid should be increased if the density of the emulsion sample correlates to a value above the upper setpoint value, and an indication that the amount of makeup acid should be decreased if the density of the emulsion sample correlates to a value below the lower setpoint value.

* * * * *